United States Patent
Lösch et al.

(10) Patent No.: US 6,797,943 B2
(45) Date of Patent: Sep. 28, 2004

(54) METHOD AND APPARATUS FOR ION MOBILITY SPECTROMETRY

(75) Inventors: Karsten Lösch, Berlin (DE); Bengt Nölting, Berlin (DE)

(73) Assignee: Siemens AG, München ( * ) Notice: Subject to any disclaimer, the term of this patent is extended or adjusted under 35 U.S.C. 154(b) by 0 days.

(21) Appl. No.: 10/139,635

(22) Filed: May 7, 2002

(65) Prior Publication Data

US 2003/0209665 A1 Nov. 13, 2003

(51) Int. Cl.⁷ .......................... H01J 49/00; H01J 49/40
(52) U.S. Cl. ...................................... 250/282; 250/287
(58) Field of Search ........................ 250/282, 283–288, 250/281, 290, 295, 296, 299, 300

(56) References Cited

U.S. PATENT DOCUMENTS

| | | | | |
|---|---|---|---|---|
| 5,218,203 A | * | 6/1993 | Eisele et al. | 250/282 |
| 5,338,931 A | * | 8/1994 | Spangler et al. | 250/287 |
| 5,905,258 A | * | 5/1999 | Clemmer et al. | 250/282 |
| 5,968,837 A | * | 10/1999 | Doring et al. | 250/282 |
| 6,000,241 A | * | 12/1999 | Ranade et al. | 65/17.2 |
| 6,225,623 B1 | | 5/2001 | Turner et al. | |
| 6,342,393 B1 | * | 1/2002 | Hofstadler et al. | 250/282 |
| 6,586,729 B2 | * | 7/2003 | Doring | 250/282 |
| 2001/0032929 A1 | * | 10/2001 | Fuhrer et al. | 250/281 |
| 2002/0017605 A1 | * | 2/2002 | Jenkins et al. | 250/287 |
| 2003/0001084 A1 | * | 1/2003 | Bateman et al. | 250/282 |
| 2003/0001087 A1 | * | 1/2003 | Fuhrer et al. | 250/287 |

FOREIGN PATENT DOCUMENTS

| | | |
|---|---|---|
| DE | 4206109 A1 | 9/1993 |
| DE | 4415014 C2 | 12/1996 |
| DE | 19609582 C1 | 5/1997 |
| DE | 19627620 C1 | 11/1997 |
| DE | 19953821 A1 | 7/2000 |
| DE | 10042394 A1 | 4/2002 |

OTHER PUBLICATIONS

Derwent Abstract for DE 19953821.
Derwent Abstract for DE 10042394A1.
Derwent Abstract for DE 19627620C1.
Derwent Abstract for DE 19609582C1.
Derwent Abstract forDE4206109A1.
Derwent Abstract for DE4415014A1.
John Gormally et al., "The Performance of an Ion Mobility Spectrometer for use with Laser Ionization", International Journal of Mass Spectrometry and Ion Processes, 107(1991) 441–451.

* cited by examiner

Primary Examiner—John R. Lee
Assistant Examiner—James P. Hughes
(74) Attorney, Agent, or Firm—Jacob Eisenberg Siemens AG (57) ABSTRACT

Molecular ions are generated by ionization, said molecular ions are accumulated in an ion reservoir that is external to the drift chamber. Than said molecular ions are dissociated into fragment ions (i.e. fragmented ions) with electromagnetic radiation or electron beams or ion beams, and said fragment ions are ion-mobility spectrometrically analyzed. In an embodiment the apparatus comprises additionally a virtual impactor and a pyrolyzer. The process of fragmentation over time are detected and analyzed, and this information is used for the differentiation of hazardous biological samples from non-hazardous biological samples.

34 Claims, 7 Drawing Sheets

METHOD AND APPARATUS FOR ION MOBILITY SPECTROMETRY

BACKGROUND OF THE INVENTION

The present invention relates to an improved method and apparatus for ion mobility spectrometry. In particular the invention provides a method and apparatus that yield a higher information content of the obtained ion-mobility spectra and a better probability of correct identification of hazardous substances and a better distinction between hazardous and non-hazardous chemical and biological agents. The method and apparatus of the invention can be used for the analysis of ions of macromolecules for environmental screening, e.g. the detection of proteins and lipids that occur in hazardous biological agents. In particular the improved method and apparatus for ion mobility spectrometry are useful for the detection of biological weapons made from viruses or bacterial spores and inorganic and organic surfactants and other chemicals, e.g. micrometer-sized dust-forming silicate particles.

Ion mobility spectrometry is a powerful analytical tool for the detection of chemical and biological hazards. Typically, in an ion mobility spectrometer (IMS) the sample is ionized, passed through an electric field and the time-of-flight of the different sample ions at atmospheric pressure is detected by an electrode detector. The disadvantage of these prior art IMS is that the false alarm rate for the detection of some chemical and biological hazards is too high for many important civil applications. Some mass spectrometers (MS) have better false alarm rates, but MS are very expensive since they require complicated vacuum technology (see e.g. U.S. Pat. No. 6,342,393). The purpose of this invention lies in an improved method and apparatus for ion mobility spectrometry to obtain a significantly improved accuracy of detection.

BRIEF SUMMARY OF THE INVENTION

In a first embodiment, an IMS is set out wherein molecular ions of the sample are dissociated into fragment ions, and in which the spectra of the fragment ions and the process of fragmentation over time are analyzed. For example, electromagnetic or electron beams may create fragmentation which increases the number of different ions that are detected by the detector of the ion-mobility spectrometer. For detection of biological hazards, the sample may be collected by a virtual impactor, partially chemically decomposed in a pyrolyzer and separated into fractions in gas chromatograph before being analyzed in the IMS. In a further embodiment of the methods and apparatuses of the invention, the interaction of the sample ions with each other over time is monitored and used to achieve a higher information content. Beyond this, in one embodiment of the methods and apparatuses of the invention, a chemical that interacts with the sample is added to the inert gas of the ion mobility spectrometer and the changes of the ion mobility spectra are monitored and used for obtaining a higher information content. This chemical can e.g. be a pH-modifier. Beyond this, in another embodiment of the methods and apparatuses of the invention, larger particles are detected with an ion-mobility spectrometer by using the reversion of the flow of the inert gas relative to the common direction and thereby dragging large particles towards the collector electrode, and using this detection to obtain a higher information content about the sample, e.g. about the presence of weapons-typical additions to spores and viruses.

In the embodiments which comprise multiple gatings, before injecting a new sample into the ionization chamber, a higher yield of collected ions may be achieved which may lead to a further improvement of signal/noise ratios. Said ion mobility spectrometers may be operated in the positive or negative ion mode or in both ion modes. The ionization of a target compound of the sample can be done directly by an ionization source that emits energy that interacts with and ionizes the target compound. Alternatively or additionally, a target compound of the sample can be indirectly ionized by an ionization source which emits energy that interacts with and ionizes an intermediate compound which, in turn, interacts with and ionizes the target compound. It should be understood that his invention has been disclosed so that one skilled in the art may appreciate its features and advantages, and that a detailed description of specific components and the spacing and size of the components is not necessary to obtain that understanding. Many of the individual components of the ion mobility spectrometers are conventional in the industry, and accordingly are only schematically depicted. The disclosure and description of the invention and the examples are thus explanatory, and various details in the construction of the equipment are not included. Alternative embodiments and operating techniques will become apparent to those skilled in the art in view of this disclosure, and such modifications should be considered within the scope of the invention, which is defined by the claims. The invention described can of-course also be used in combination with the known prior art variants of ion-mobility spectrometry.

BRIEF DESCRIPTION OF THE SEVERAL VIEWS OF THE DRAWINGS

The invention will be described in conjunction with certain drawings which are for the purpose of illustrating the preferred and alternate embodiments of the invention only, and not for the purpose of limiting the same, and wherein.

DETAILED DESCRIPTION OF THE INVENTION

Figure 1:
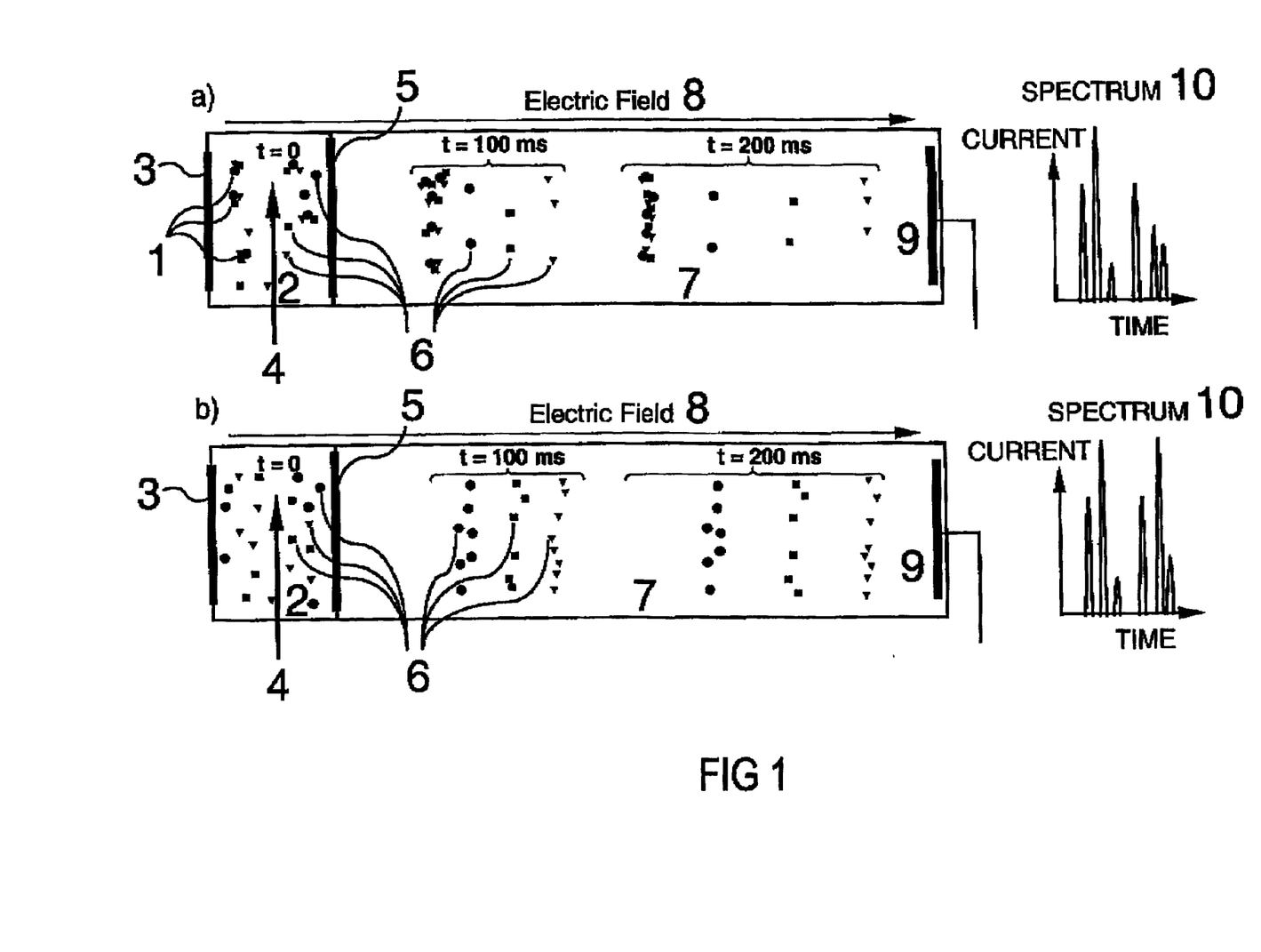
FIG. 1 is a schematic structural view showing of an apparatus for ion mobility spectroscopy with a infrared laser for fragmentation.

FIG. 1 shows a schematic structural view showing of an apparatus for ion mobility spectroscopy with a infrared laser for fragmentation. The sample 1 is injected into the ionization chamber 2 and ionized by the source of ionization 3 which may be e.g. a radioactive source such as $^3$H, $^{53}$Ni, or $^{241}$Am, UV or VUV light, or an electrical discharge (non-radioactive electron source). For example, when using a $^{53}$Ni foil as source of ionization and air as drift gas, the primary ions are mainly short-living $N_2^+$, $NO^+$ and $O_2^+$. These $N_2^+$, $NO^+$ and $O_2^-$ rapidly react with traces of water in the drift gas to form clusters of the types $N_2^+(H_2O)_x$, $NO^+(H_2O)_y$, and $O_2^+(H_2O)_z$, which then cluster with the molecules and clusters of the sample. The ionization chamber 2 serves as ion reservoir. After injection of the sample into the ionization chamber 2, some of the sample molecules and sample ions start to dissociate into fragment molecules and fragment ions due to interaction with the light from an infrared LASER 4. With the help of a gating pulse which is applied to the gate 5, the fragment ions 6 from the ionization chamber 2 are transferred into the drift chamber 7 where the fragment ions 6 are accelerated by an electric field 8. The time of flight of the fragment ions 6 in the gaseous phase is measured with the help of a collector 9. Since different fragment ions 6 have different mobilities in the gas of the drift tube, they result in distinct peaks in the IMS spectrum 10. Several measurements, without interrupting the dissociation reaction caused by the LASER 4, are done before injecting a new sample into the ionization chamber 2. The indicated time points, 0, 100 ms, and 200 ms, respectively, refer to the time after application of a gating pulse. In order to reduce the noise, the ion mobility spectrometer is enclosed in a grounded copper foil. The collector 9 is connected with a $10^{10}$-V/A pre-amplifier via a cable of only a few mm length. The feedback resistor of the pre-amplifier was selected for a low noise level. The voltage supply for the guard rings of the drift tube is stabilized to better than 0.1% rms, a) after a short period of time for fragmentation, e.g. 1 second, b) after a long time of fragmentation, e.g. 5 seconds; significant fragmentation has occurred and accordingly characteristic changes of the heights of some peaks in the ion-mobility spectra are observed. The information of the spectra at the beginning, i.e. when the sample is still non-fragmented, and the characteristic changes of spectra over time due to fragmentation are used to characterize the sample. In particular, the sample is evaluated for a hazardous biological content. For example, the measured spectra are correlated with a data base which contains spectra of non-fragmented samples and their changes due to fragmentation wherein the correlation procedure includes the use of small distortions of the drift time of the spectra.

Figure 2:
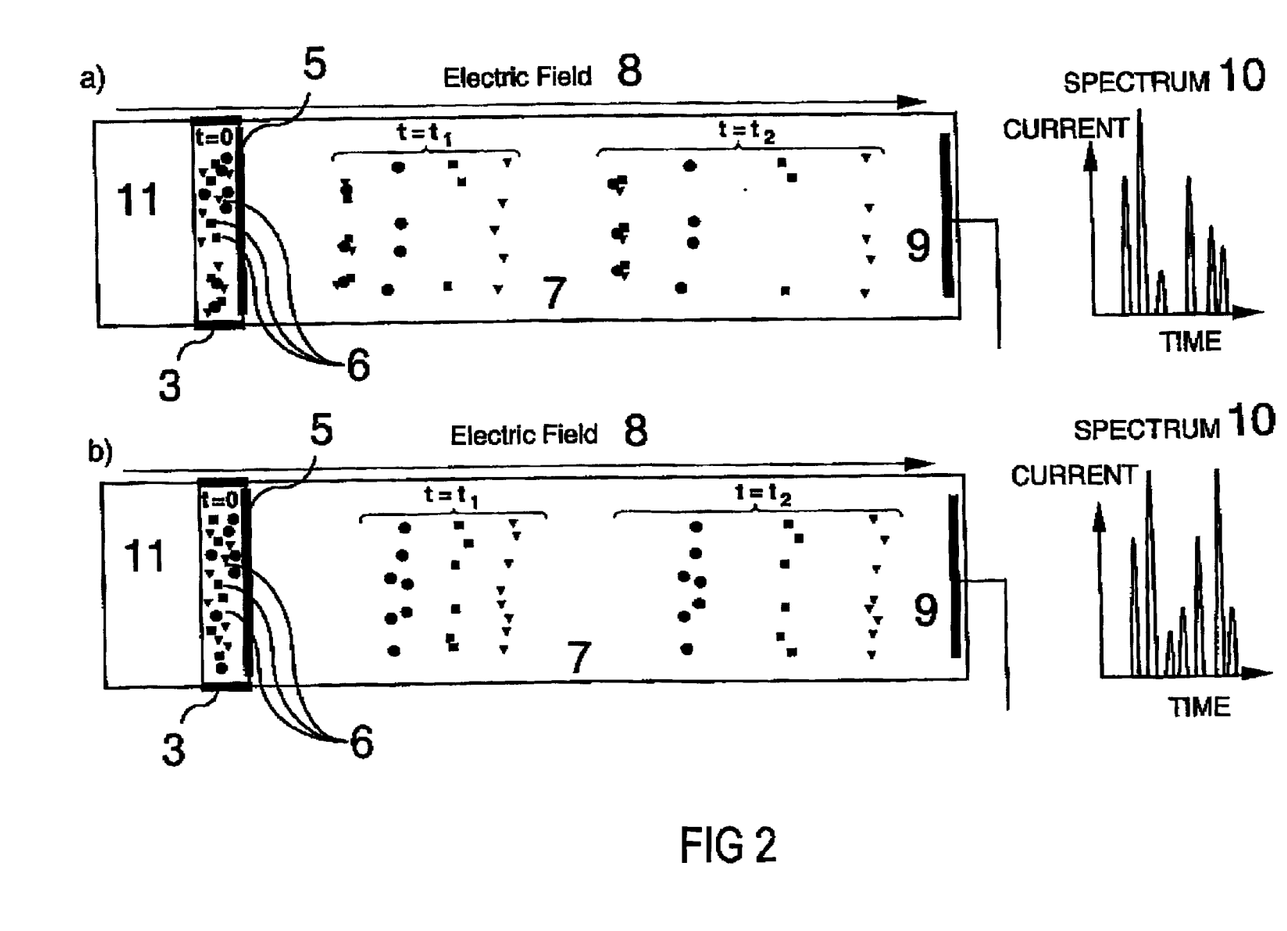
FIG. 2 is a schematic structural view showing of an apparatus for ion mobility spectroscopy with a UV lamp for fragmentation.

The operation of the apparatus in FIG. 2 is similar to FIG. 1, but here the fragmentation is done with light from an UV or vacuum-UV (VUV) lamp 11. Alternatively, the fragmentation may be done with electron beams (electron-ionization or electron bombardment) or ion beams (ion bombardment) or other methods. For example, electron beams may be generated in vacuum and released into the gaseous medium of the ionization chamber 2 through a thin membrane. The indicated time points, 0, $t_1$, and $t_2$, respectively, refer to the time after application of a gating pulse. Depending on the methods of ionization and fragmentation, the amount of humidity in the drift chamber 7 may greatly affect the sensitivity of the spectrometer. That is why in some variants of this design, the humidity may be controlled by pumping the drift gas through a molecular sieve. After a short period of time for fragmentation (a), the spectra show little change. After a long time of fragmentation (b), significant fragmentation has occurred and accordingly characteristic changes of the heights of some peaks in the ion-mobility spectra are observed. The operation of the spectrometer may comprise the following steps: (i) The sample is continuously collected from different locations via a pump and several tubes with 2 mm diameter and a few m length. (ii) The sample 1 is passed through a virtual impactor which selects a size range of 0.5–8 $\mu$m and discards particle sizes which are smaller than 0.5 $\mu$m and larger than 8 $\mu$m. (iii) The collected sample is stored in a container having a 20 mL volume. (iv) After 2 minutes of collection and storage, the complete sample is transferred from the container into a pyrolyzer which causes partial decomposition of the sample. (v) The product of the pyrolyzation reaction at 350° C. within the time range of 5 s–8 s after transfer to the pyrolyzer is transferred to the ionization chamber of the ion-mobility spectrometer. (vi) In the ionization chamber 2, the sample is ionized and fragmented. (vii) The first gating pulse is applied a few milliseconds after transfer of the sample to the gate 5. (viii) The first ion-mobility spectrum is recorded and stored on a computer. This spectrum corresponds to the essentially non-fragmented sample. (ix) Several more ion-mobility measurements are performed on the sample over a period of 30 seconds. The spectra obtained correspond to different degrees of fragmentation of the sample and are also stored on the computer. (x) By this way the spectra of the sample with different degrees of fragmentation, from essentially non-fragmented to essentially completely fragmented, are obtained. (xi) The information from the spectrum of the almost non-fragmented sample and the information from the transitions of several peaks in the course of fragmentation are used for the analysis of the sample. In particular neuronal networks are used for the distinction between hazardous and non-hazardous samples. Because the information content of the spectra is much higher than in the prior art ion mobility spectrometry of biological agents, the false alarm rate is significantly reduced.

Figure 3:
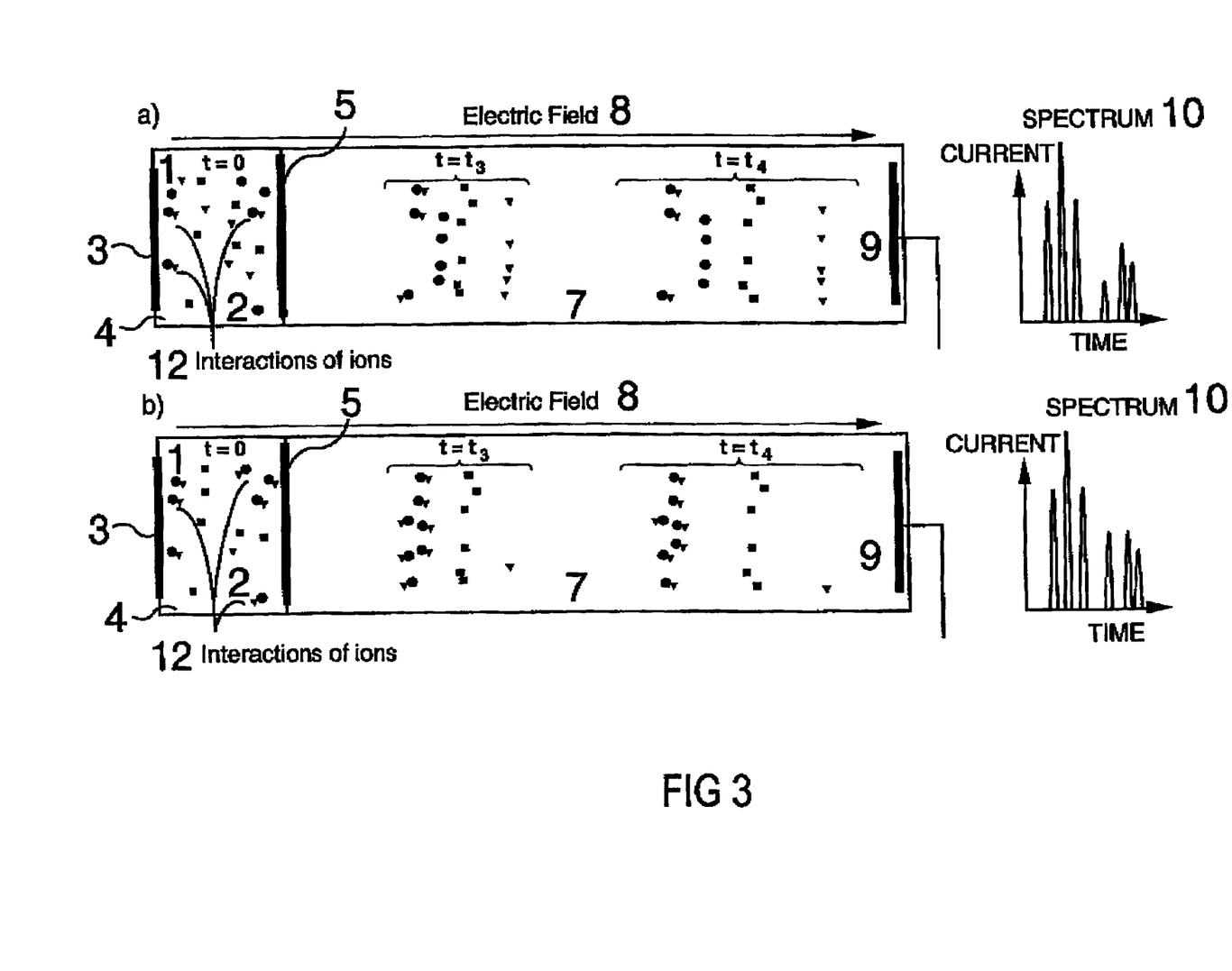
FIG. 3 is a schematic structural view showing of an apparatus for ion mobility spectroscopy with a infrared laser for fragmentation and with several gating pulses.

FIG. 3 shows a schematic structural view showing of an apparatus for ion mobility spectroscopy with a infrared laser for fragmentation and with several gating pulses. The sample is injected into the ionization chamber 2 and ionized by the source of ionization 3 which may be e.g. a radioactive source such as e.g. $^3$H, $^{53}$Ni, or $^{241}$Am, UV or VUV light, or an electrical discharge (non-radioactive electron source). After ionization, some of the sample ions start to interact with each other 12. After the fragmentation several gating pulses are applied to the gate 5 and several measurements of ion-mobility spectra 10 are made before a new sample is injected into the ionization chamber 2. Thus, successive ion-mobility spectra follow the interaction of ions in the ionization chamber 2. This change of the spectra over time is used for a better characterization of the sample, a) after a short period of time of interaction, b) after a long time of interaction in the ionization chamber 2, characteristic changes of the heights of some peaks in the ion-mobility spectra are observed and used for the identification of the sample.

Figure 4:
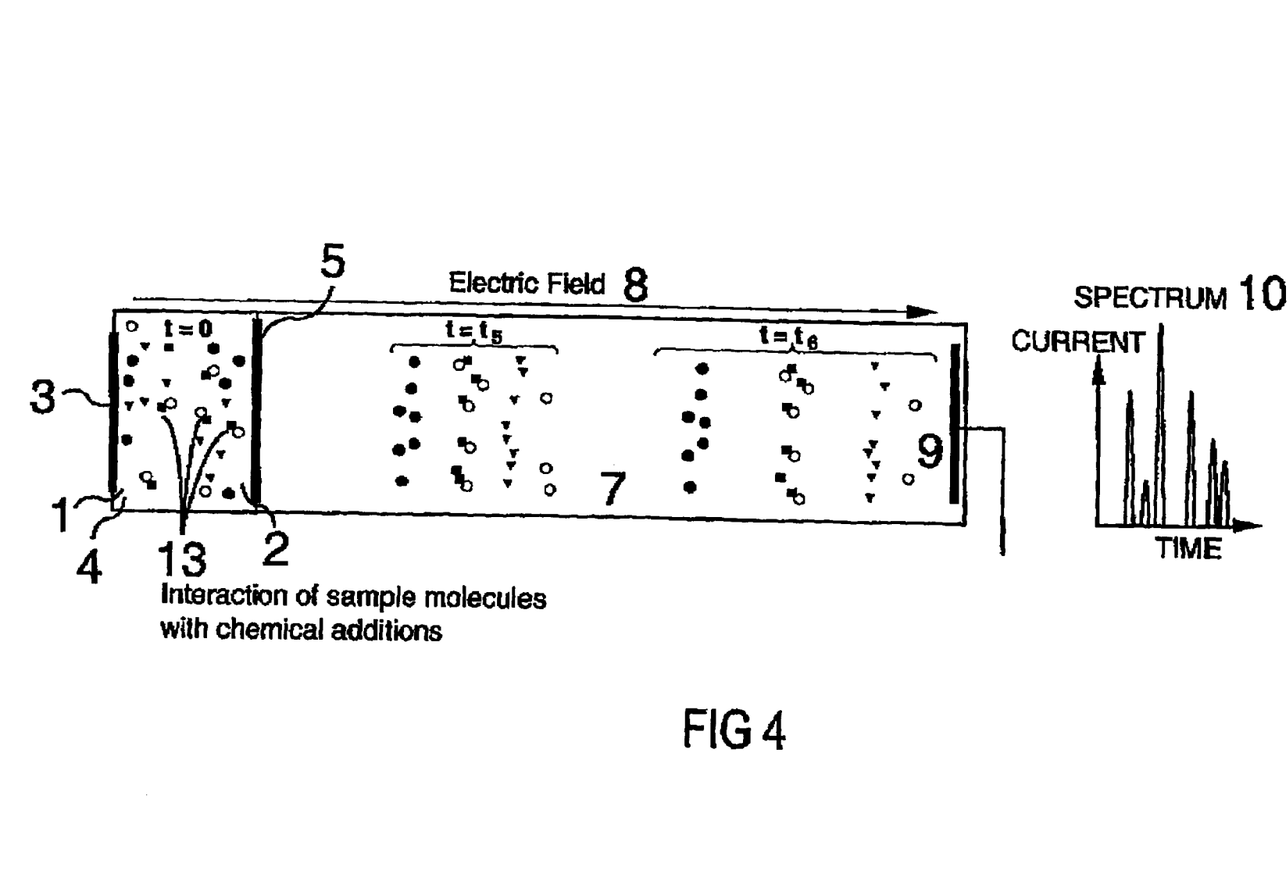
FIG. 4 is a schematic structural view showing of an apparatus for ion mobility spectroscopy with a infrared laser for fragmentation and interaction with chemical addition.

FIG. 4 shows a schematic structural view showing of an apparatus for ion mobility spectroscopy with a infrared laser for fragmentation and interaction with chemical additions. The biological sample is injected into the ionization chamber 2 and ionized by the source of ionization 3 which may be a radioactive source such as e.g. $^3$H, $^{53}$Ni, or $^{241}$Am, UV or VUV light, or an electrical discharge (non-radioactive electron source). A chemical addition was added to the inert gas of the IMS or already to the sample in the pyrolysis tube. The chemical addition may be e.g. HCl or $NH_3$. This chemical addition can interact 13 with the sample molecules and sample ions and thereby causing specific changes of the ion-mobility spectra 3 of the fragmentation ions. In particular, in the presence of some water vapor, $NH_3$ can bind to fatty acids of virus envelopes. Acidic additions, e.g. HCl, and basic additions in the presence of some water vapor, can change the pH of proteins and polypeptides, and consequently their charge state and thus their ion-mobility spectra. The changes of the ion-mobility spectra caused by the presence of the chemical additions help to identify and characterize the sample.

Figure 5:
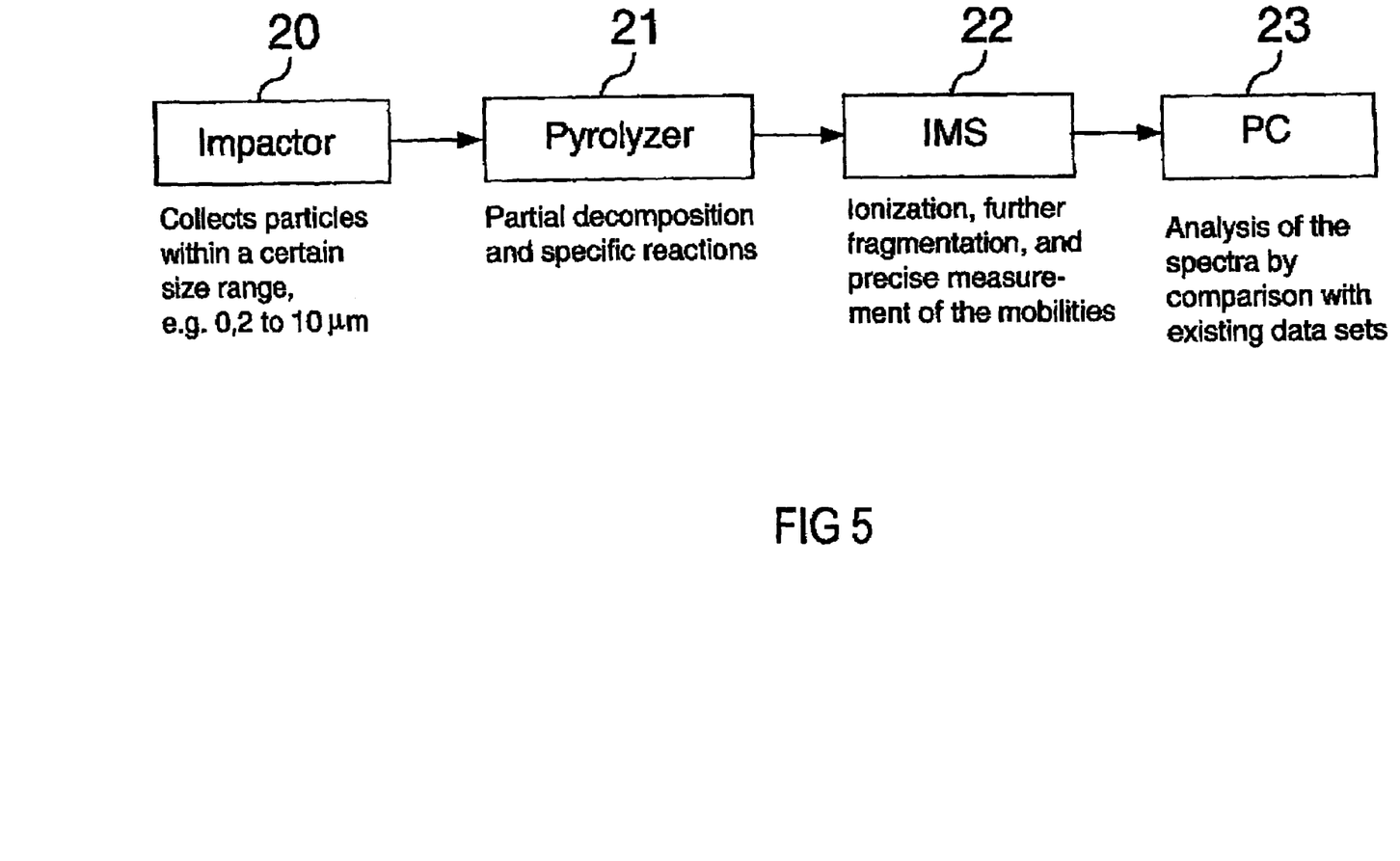
FIG. 5 is a block diagram of an apparatus for ion mobility spectroscopy.
Figure 6:
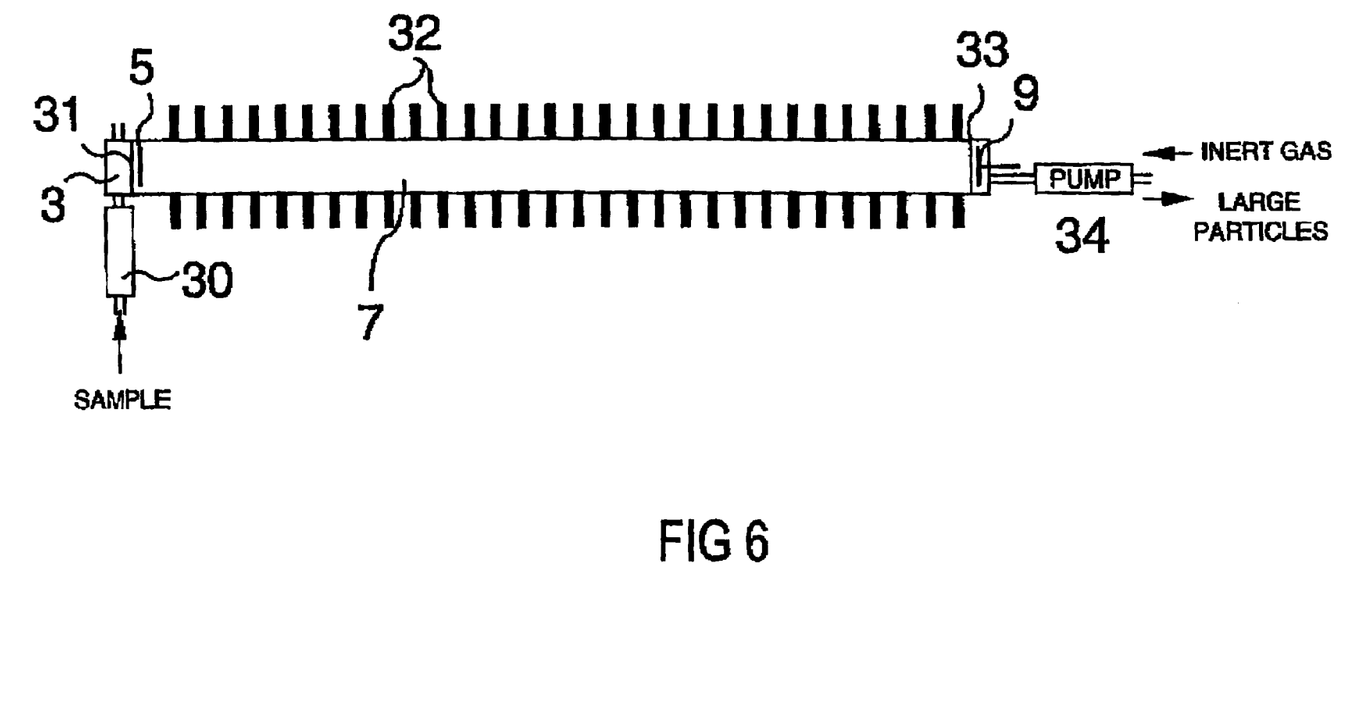
FIG. 6 is a schematic structural view showing of an apparatus for ion mobility spectroscopy with 30 guard rings and 2 pumps.
Figure 7:
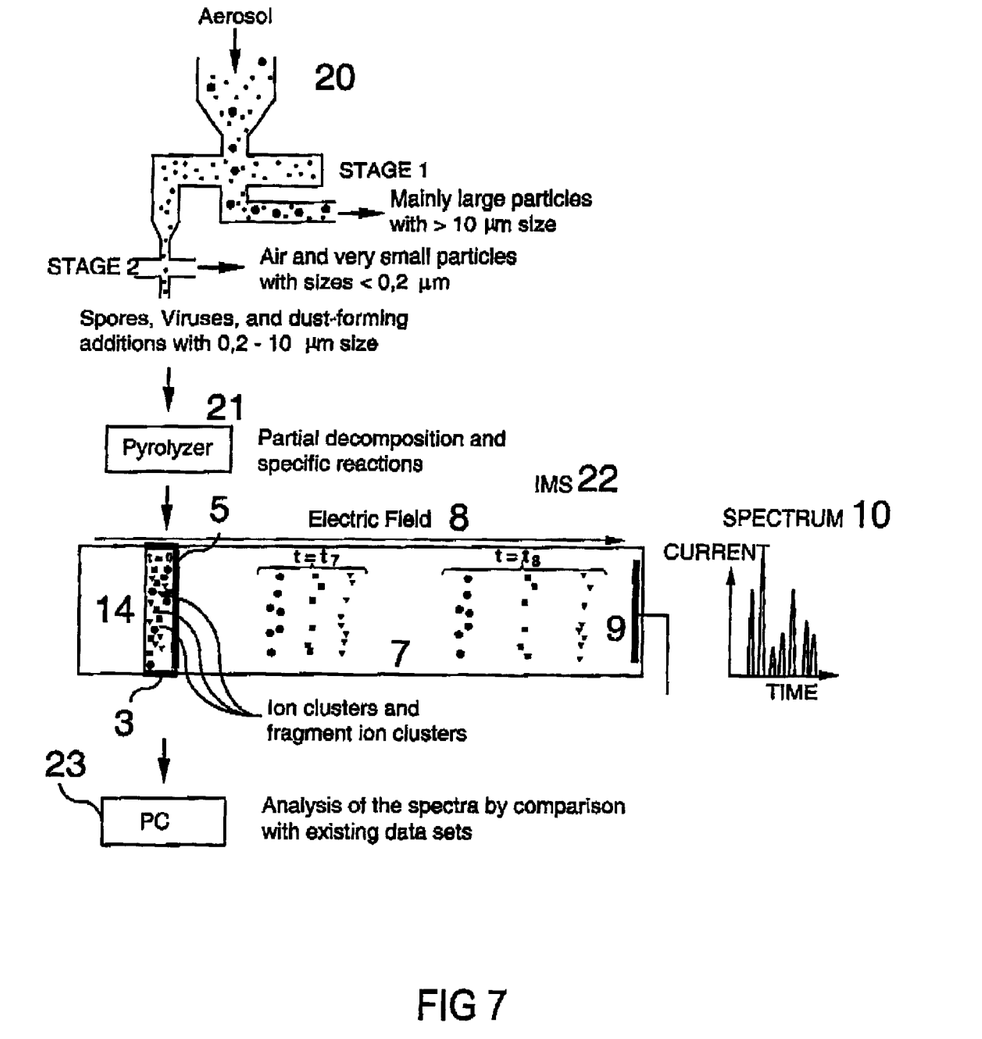
FIG. 7 is a schematic structural view showing of an apparatus for ion mobility spectroscopy with an impactor and a pyrolyzer.

FIG. 5 shows a block diagram of an apparatus for ion mobility spectroscopy. A virtual impactor 20 is e.g. continuously operated and serves for selecting and concentrating a certain size range of particles, e.g. 0.2 $\mu$m (e.g. single influenza virus or other pathogen) to 10 $\mu$m (e.g. several spores of anthrax bound to a dust particle or other pathogen). Particle size and size distribution offer too little information to unambiguously identify biological hazards in the presence of significant amounts of interferrents of non-hazardous substances. That is why the biological agents are collected and, from time to time, injected into a pyrolyzer 21 where they are partially decomposed into chemical components. The output from the pyrolyzer 21 is then transferred to the ion mobility spectrometer (IMS) 22 where it is ionized and further decomposed. In this way a very detailed ion-mobility spectrum with a large number of peaks is obtained which represents a finger print of the biological agent. Sample injection into the pyrolyzer and sample transfer from the pyrolyzer to the IMS are organized in such a way that a chemical pre-selection is performed, i.e. that only some of the products of the pyrolysis are analyzed in the IMS, e.g. lipids, polysaccarides, and weapons-typical additions to bacterial spores. A computer 23 analyzes the IMS spectra and as well their changes due to fragmentation of ions. In this way a large amount of information about the biological agents is obtained which allows the distinction between hazardous and non-hazardous agents.

FIG. 6 shows an ion mobility spectrometer with 30 guard rings 32 and 2 pumps. A first pump 30 conveys the sample into the ionization chamber 2. The operation of an inert gas pump 34 at the other end of the drift chamber 7 can be reversed which leads to the possibility of detection of very large particles, e.g. weapons-typical micrometer-sized additions to bacterial spores. The insulating layers between the guard rings 32 are made from an inert polymer. Guard rings 32 and insulating layers are held together with 3 screws which each attached to a spring in order to exert a constant pressure on the guard rings 32 and insulating layers.

FIG. 7 shows a schematic structural view showing of an apparatus for ion mobility spectroscopy with an impactor and a pyrolyzer. For example, a two-stage virtual impactor 20 is operated with a flow rate of a few 100 L/min and collects and concentrates particles with sizes from about 0.2 to 10 micrometers. The concentrated aerosol is transferred to the pyrolyzer 21 which is operated at about 350° C. After application of a few seconds of pyrolysis, the partially decomposed sample enters the ionization chamber 2 of the ion-mobility spectrometer 22. The source of ionization 3, e.g. a $^{53}$Ni foil, serves for the ionization of the partially decomposed sample. The sample ions formed by this process are then fragmented with electron beams which are generated by the electron beam generator 14. Sample ions and fragment ions interact with each other and form various clusters. The fragmentation and clustering processes cause specific changes of the ion-mobility spectra 10 over time. Several ion-mobility spectra in the positive and negative ion modes are recorded before a new sample is injected into the ionization chamber 2. The specific changes of the spectra over time are used for the automatized differentiation of hazardous from non-hazardous samples with the help of software and computer 23.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for ion-mobility spectrometry of a sample, comprising the steps of:

(a) generating molecular ions by ionization and accumulating said molecular ions in an ion reservoir that is external to a drift chamber of an ion-mobility spectrometer; and (b) exposing said molecular ions in said ion reservoir to a source of energy for a time sufficient for dissociation of said ions into fragment ions prior to ion-mobility analysis in the drift chamber of the ion-mobility spectrometer, wherein said exposing results in production of multiple charge states of fragment ions, and a degree of said dissociation of said ions into fragment ions is more than 50% for some of said ions and changes of ion-mobility-spectra due to fragmentation by said more than 50% are used for characterization of the sample.

2. The method of claim 1, wherein said source of energy comprises one of UV radiation, VUV radiation, and photo ionization.

3. The method of claim 1, wherein said source of energy comprises one of electron beams, electron bombardment, electro spray, electron-ionization, corona discharge, and glow discharge.

4. The method of claim 1, wherein said source of energy comprises one of ion beams and ion bombardment.

5. The method of claim 1, wherein said source of energy comprises radioactive emission.

6. The method of claim 1, wherein said source of energy comprises plasma.

7. The method of claim 1, wherein said source of energy comprises infrared radiation.

8. The method of claim 1, wherein said exposing of said ions in said ion reservoir to a source of energy is performed during accumulation of said ions in said ion reservoir.

9. The method of claim 1, wherein said exposing of said ions in said ion reservoir to a source of energy is performed after accumulation of said ions in said ion reservoir.

10. The method of claim 1, wherein said source of energy is electron beams which are generated in vacuum and released to non-vacuum parts of said ion-mobility spectrometer through a membrane.

11. The method of claim 1, wherein said source of energy comprises UV radiation having a wavelength between about 120 nm and about 300 nm.

12. The method of claim 1, wherein said source of energy comprises coherent infrared radiation.

13. The method of claim 1, wherein said ion-mobility spectrometer is connected with a pyrolyzer or gas chromatograph.

14. The method of claim 13, wherein only select fractions of the output of said pyrolyzer or gas chromatograph are transferred to said ion-mobility spectrometer.

15. The method of claim 13, wherein said pyrolyzer or gas chromatograph is connected with a virtual impactor.

16. The method of claim 1, wherein the drift chamber of said ion-mobility spectrometer is operated at a pressure between about 500 and about 5000 torr.

17. The method of claim 1, wherein the drift chamber of said ion-mobility spectrometer is operated at a pressure between about 10 and about 500 torr.

18. The method of claim 1, wherein the generation of ions of the sample in said ion-mobility spectrometer is achieved using a radioactive source comprises one of $^3$H, $^{53}$Ni, $^{241}$Am, UV light, VUV light, an electrical discharge, a corona discharge, and electrospray.

19. The method of claim 1, wherein said generating said molecular ions by ionization involves an ionization of inert-gas molecules of said ion-mobility spectrometer and clustering of inert-gas ions with one of sample molecules, sample-molecule clusters, and sample-molecule fragments.

20. The method of claim 1, wherein said ion-mobility spectrometer has a drift chamber with a length between about 40 cm and about 60 cm.

21. The method of claim 1, wherein the substance which is analyzed in said ion-mobility spectrometer is pyrolyzed bioweapons-grade material.

22. A method for ion-mobility spectrometry of a sample, comprising the steps of:
   (a) generating molecular ions by ionization and accumulating said molecular ions in an ion reservoir that is external to a drift chamber of an ion-mobility spectrometer;
   (b) exposing said molecular ions in said ion reservoir to a source of energy for a time sufficient for dissociation of said ions into fragment ions prior to ion-mobility analysis in the drift chamber of the ion-mobility spectrometer, wherein said exposing results in production of multiple charge states of fragment ions, and wherein further micrometer-sized and sub micrometer-sized particles are detected according to the following steps:
   (c) generating particle ions by ionization;
   (d) extracting gas from the drift chamber whereby movement of said particle ions towards a collector in the drift chamber of said ion-mobility spectrometer is increased; and
   (e) measuring and analyzing the collector current generated by particle ions.

23. The method of claim 22, wherein said particles have sizes between about 100 nm and about 10 $\mu$m.

24. The method of claim 22, wherein said particles have sizes between about 2 $\mu$m and about 10 $\mu$m.

25. The method of claim 22, wherein said particles are bioweapons-grade micrometer-sized particles with attached spores or viruses.

26. The method of claim 22, wherein said particles are bioweapons-grade silicate particles with attached spores or viruses.

27. The method of claim 22, wherein said particles comprise of inorganic compounds that are partially coated with organic compounds.

28. The method of claim 22, wherein said particles comprise at least one pathogen.

29. The method of claim 22, wherein the sample is passed through a virtual impactor prior to analysis in said ion-mobility spectrometer.

30. The method of claim 22, wherein said generating said particle ions by ionization further comprises an ionization of inert-gas molecules of said ion-mobility spectrometer and clustering of inert-gas ions with said particle.

31. The method of claim 1, wherein an electric field of said drift chamber has a strength between about 50 V/cm and about 5000 V/cm and is applied using more than 5 electrodes or guard rings.

32. The method of claim 1, wherein said ion-mobility spectrometer is connected with a pyrolyzer and gas chromatograph.

33. The method of claim 13, wherein only select fractions of the output of said pyrolyzer and gas chromatograph are transferred to said ion-mobility spectrometer.

34. The method of claim 13, wherein said pyrolyzer and gas chromatograph is connected with a virtual impactor.

* * * * *